(12) United States Patent
Kim et al.

(10) Patent No.: US 6,824,510 B2
(45) Date of Patent: Nov. 30, 2004

(54) MICRO ROBOT

(75) Inventors: Byungkyu Kim, Seoul (KR); Kyoung-Dae Kim, Seoul (KR); Seunghak Lee, Seoul (KR); Yeh-Sun Hong, Seoul (KR); Soo Hyun Kim, Daejeon (KR); Jong-Oh Park, Seoul (KR)

(73) Assignee: Korea Institute of Science and Technology (KR)

( * ) Notice: Subject to any disclaimer, the term of this patent is extended or adjusted under 35 U.S.C. 154(b) by 238 days.

(21) Appl. No.: 10/136,888

(22) Filed: May 1, 2002

(65) Prior Publication Data
US 2002/0173700 A1 Nov. 21, 2002

(30) Foreign Application Priority Data
May 19, 2001 (KR) .......................... 2001-27496

(51) Int. Cl.⁷ ................................ A61B 1/00
(52) U.S. Cl. .................. 600/114; 600/160; 600/101; 901/1; 348/84
(58) Field of Search ................ 600/101, 160, 600/114; 901/1, 47; 348/82, 84, 85; 73/865.8; 604/95.01

(56) References Cited

U.S. PATENT DOCUMENTS

| | | | | |
|---|---|---|---|---|
| 4,852,391 A | * | 8/1989 | Ruch et al. ............... 73/40.5 R |
| 5,142,989 A | * | 9/1992 | Suzumori et al. ......... 104/138.2 |
| 5,345,925 A | | 9/1994 | Allred, III et al. | |
| 5,493,988 A | * | 2/1996 | Kollberg ...................... 114/106 |
| 5,662,587 A | * | 9/1997 | Grundfest et al. ........... 600/114 |
| 6,071,234 A | * | 6/2000 | Takada ........................ 600/114 |
| 6,240,312 B1 | * | 5/2001 | Alfano et al. ................ 600/476 |
| 6,512,345 B2 | * | 1/2003 | Borenstein et al. ..... 318/568.12 |
| 6,648,814 B2 | * | 11/2003 | Kim et al. ................... 600/114 |
| 2003/0017779 A1 | | 1/2003 | Sakai | |
| 2003/0088152 A1 | * | 5/2003 | Takada ........................ 600/114 |
| 2003/0092353 A1 | | 5/2003 | Liu | |
| 2003/0092964 A1 | * | 5/2003 | Kim et al. ................... 600/101 |

* cited by examiner

Primary Examiner—John P. Leubecker
(74) Attorney, Agent, or Firm—Ostrolenk, Faber, Gerb & Soffen, LLP

(57) ABSTRACT

A micro robot driving system for endoscope can move a micro robot forward, backward or changing the direction by transmitting rotation force generated by a driving means to a worm gear or a gear tooth shaped belt by a worm. The micro robot driving system in accordance with the present invention includes a micro robot body, rotational force transmitting means installed in the body, for transmitting rotational force generated by driving means and movement means which is connected with the rotational force transmitting means, protruded from the body, for moving the body by rotational force transmitted by the rotational force transmitting means.

18 Claims, 13 Drawing Sheets

MICRO ROBOT

BACKGROUND OF THE INVENTION

1. Field of the Invention

The present invention relates to a micro robot driving system for endoscope.

2. Description of the Background Art

A micro endoscope robot is a micro robot equipped with a camera for photographing internal organs, a micro twizer for biopsy of tissues, and a communication module for transmitting images of internal organs so that a doctor can examine the internal organs. If this kind of micro robot is developed, simple surgeries and medicine injections are possible as well as endoscope of a stomach, small intestine or large intestines without giving much pain to a patient.

One of the existing endoscope is called an inch-worm type micro robot. This micro robot moves by being supported on walls of a small intestine or large intestine with a clamper that is inflated by air.

To move a robot by the method, the body of the robot and a portion for fixing to the circumference are required and on the condition that the portion is fixed, the robot can move by repeating the method of holding out one portion of the robot body and abutting it on the front portion again.

The method can be valid under the circumstance of having a solid characteristic such as a pipe but under the pliable circumstance such as intestines in a human body the characteristic is very inferior since the abutted portion is not fixed well.

Also, in case of increasing supporting force severely, the soft intestine wall can be damaged.

SUMMARY OF THE INVENTION

Therefore, an object of the present invention is to provide a micro robot driving system which is capable of moving forward, backward or changing the direction by transmitting rotation force generated by a driving means to a worm gear or a gear tooth shaped belt by installing a worm in the body in driving the micro robot to move.

Also, the present invention provides a micro robot driving system further including the body fixing means for preventing the micro robot from shaking in case the micro robot stops in a position to perform its operation such as examining and taking tissues.

To achieve these and other advantages and in accordance with the purpose of the present invention, as embodied and broadly described herein, there is provided a micro robot driving system comprising a micro robot body rotational force transmitting means installed in the body, for transmitting rotational force generated by driving means and movement means which is connected with the rotational force transmitting means, protruded from the body, for moving the body by rotational force transmitted by the rotational force transmitting means.

Also, the present invention provides a micro robot driving system additionally including a body fixing means which is positioned at the both ends of the body for fixing the body on the inner wall of intestines.

Also, the present invention provides a micro robot driving system comprising a plurality of micro robot bodies, rotational force transmitting means installed in the respective bodies, for transmitting rotational force generated by driving means and movement means which is connected with the rotational force transmitting means, protruded from the respective bodies, for moving the respective bodies by rotational force transmitted by the rotational force transmitting means, and wherein the respective bodies are connected by body connection means each other.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1A:
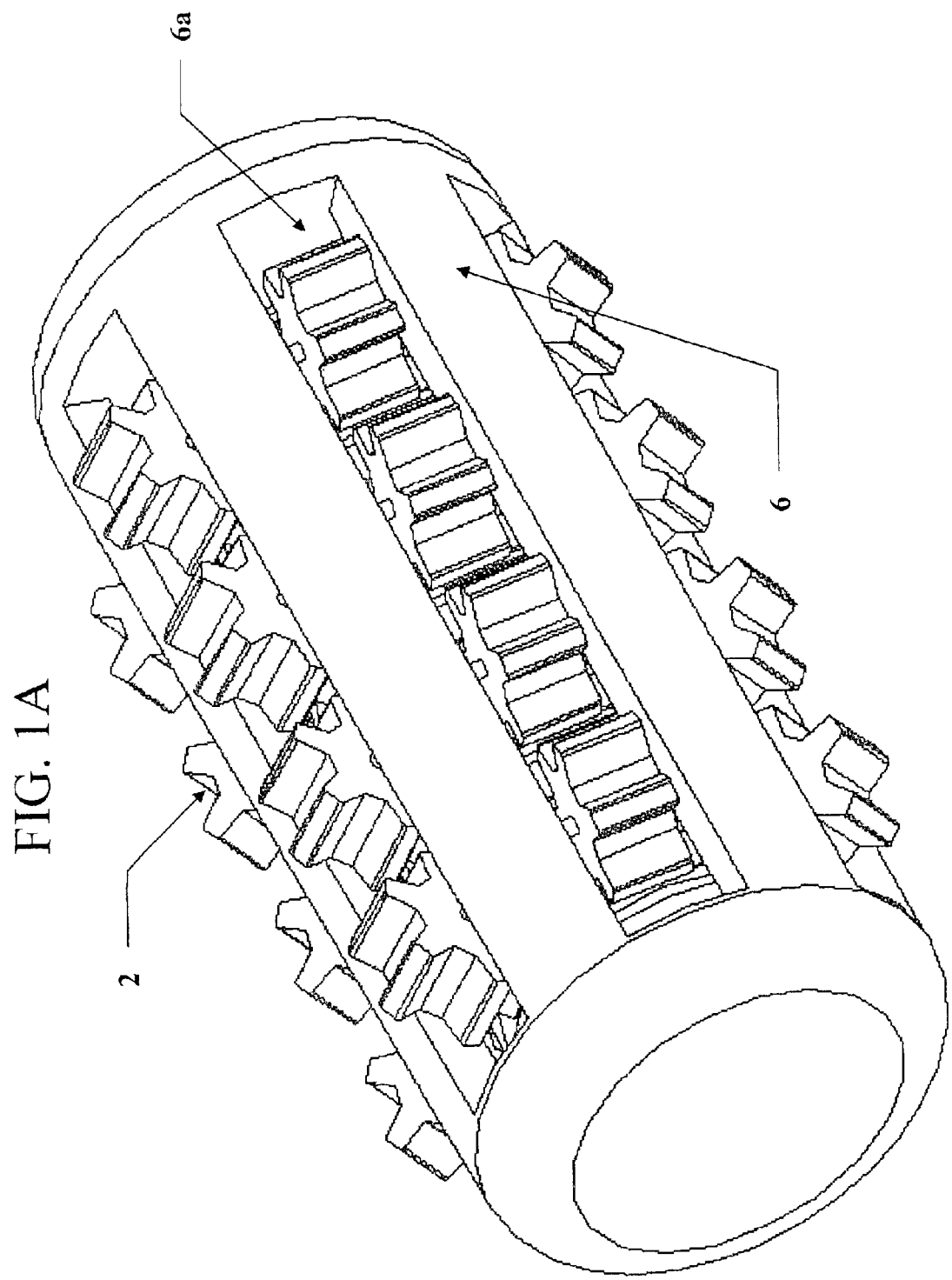
FIG. 1A is a perspective view showing a micro robot driving system having a worm gear as a first embodiment in accordance with the present invention.
Figure 1B:
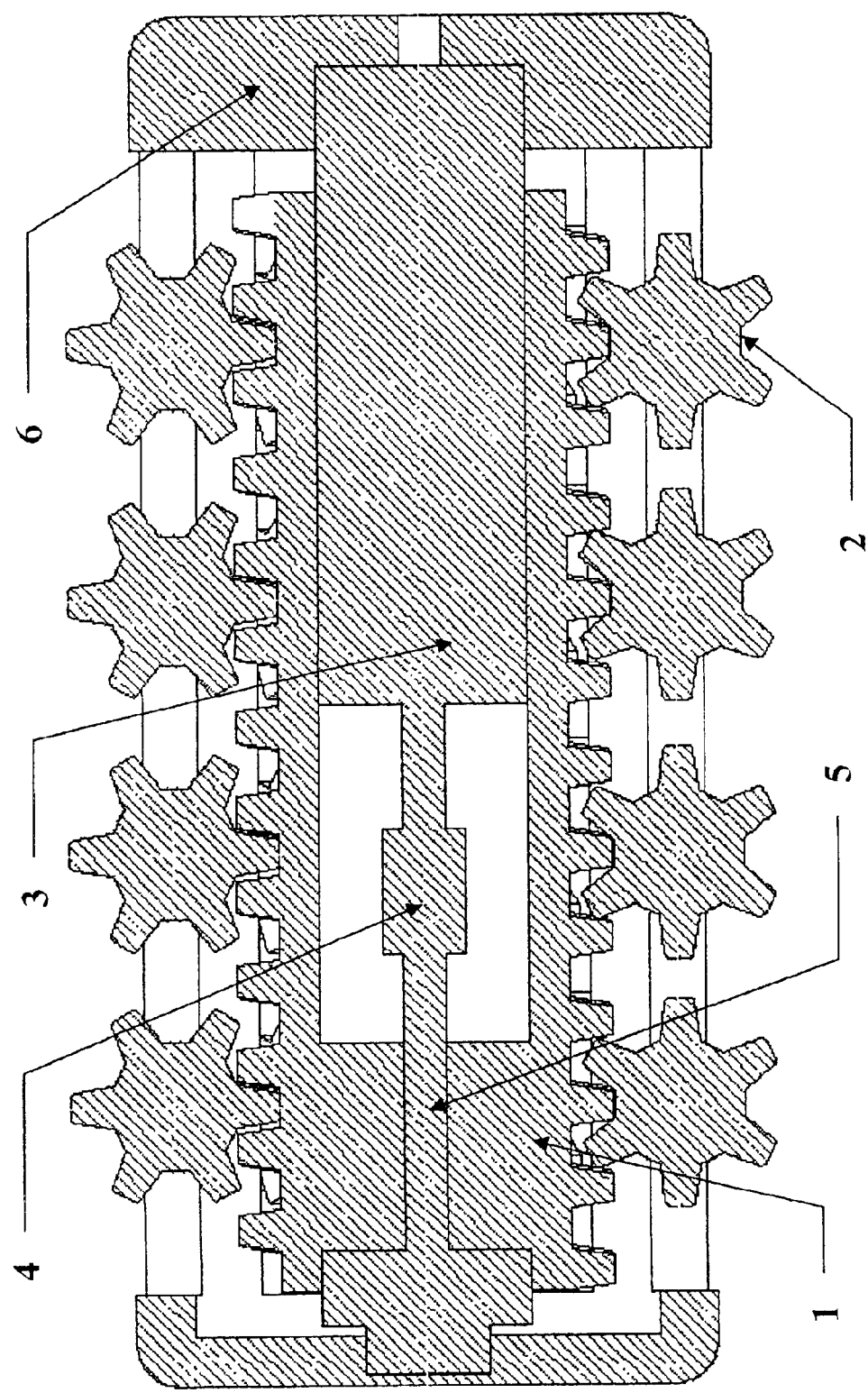
FIG. 1B is a sectional view showing a micro robot driving system having a worm gear as a first embodiment in accordance with the present invention.

FIGS. 1A and 1B are a perspective view and a sectional view showing a micro robot driving system having a worm gear as a first embodiment in accordance with the present invention.

The micro robot driving system having a worm gear according to the first embodiment is composed of a body 6 having a plurality of slots 6a formed in the longitudinal direction, driving means installed in the body 6, for generating rotational force, that is, driving means including driving apparatus 3 connected with a driving shaft 5 by a coupling 4, rotation transmitting means installed in the body 6, for transmitting the rotational force generated by the driving means, that is, worm 1, movement means positioned in the body protruding the respective slots 6a of the body, for moving the body by the rotational force transmitted by the rotational force transmitting means, that is, a plurality of worm gears 2. The movement means which is a worm gear is installed in the body rotatably.

The driving apparatus 3 is composed of a motor or an actuator for generating rotational power and the driving force of the actuator is transmitted to the worm 1 positioned in the longitudinal direction of the body 6 of the micro robot through the driving shaft 5 connected with the driving apparatus 3 by the coupling 4 for transmitting power. The rotational power can be transmitted to the plurality of worm gears positioned radially in the circumferential direction of the worm 1 and accordingly, the micro robot can move forward or rearward in accordance with the rotation of the worm gears 2. Here, the plurality of worm gears positioned around the worm 1 as the movement means can be in gear with the worm 1 by receiving the upright rotational movement of the worm 1 so that the micro robot can convert the movement direction transversely.

Figure 2A:
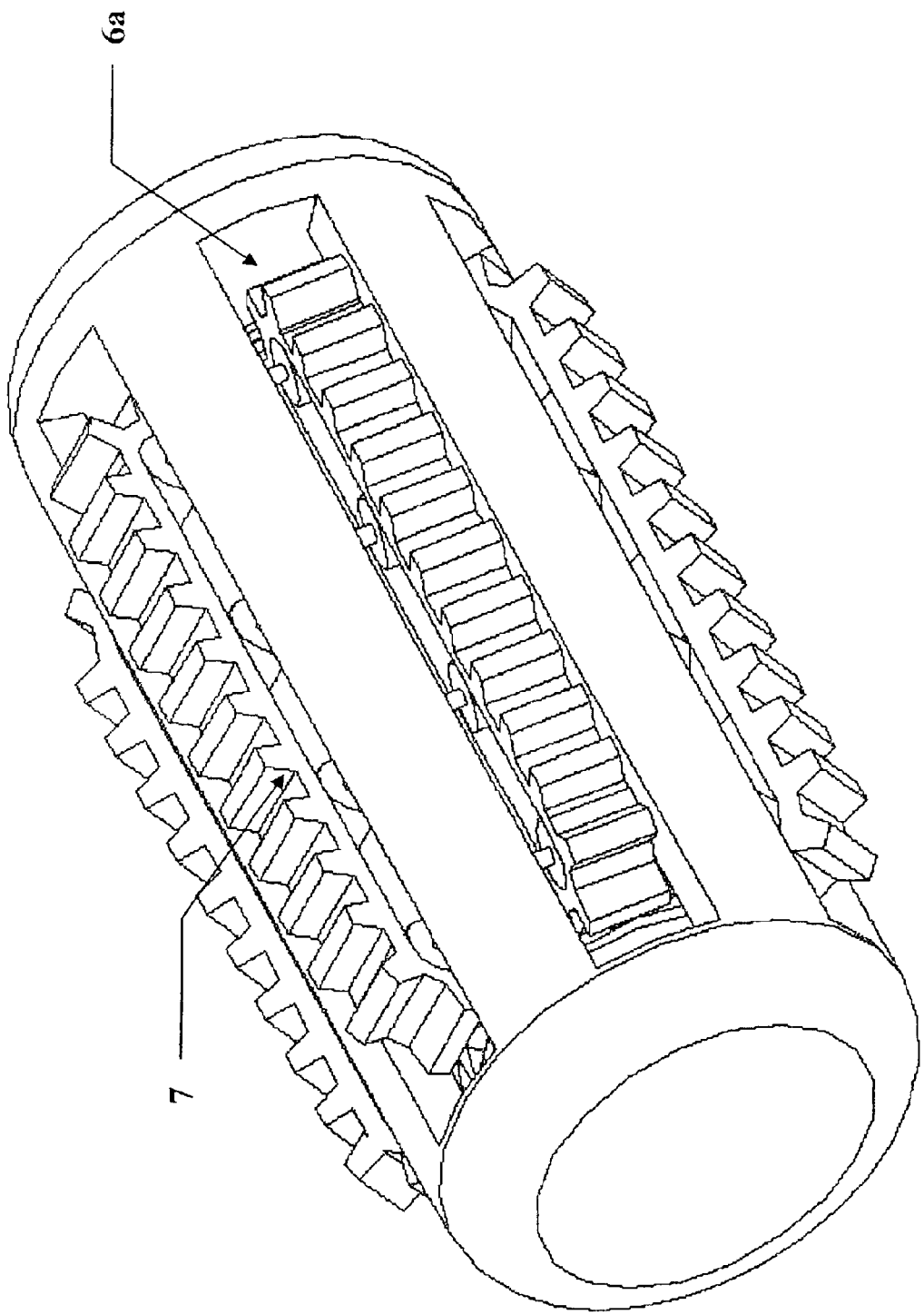
FIG. 2A is a perspective view showing a micro robot driving system having a gear tooth shaped belt as a second embodiment in accordance with the present invention.
Figure 2B:
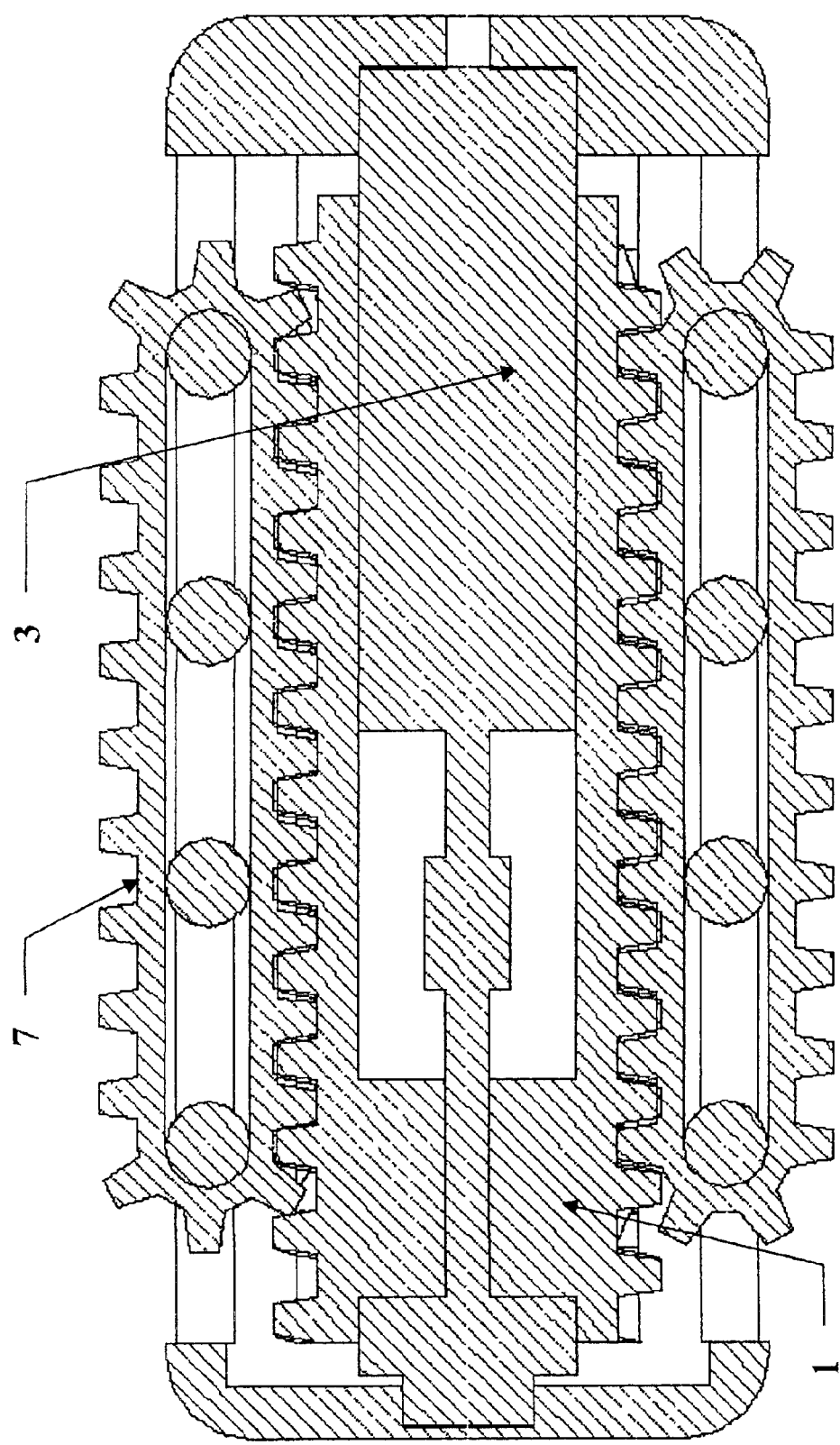
FIG. 2B is a sectional view showing a micro robot driving system having a gear tooth shaped belt as a second embodiment in accordance with the present invention.

FIGS. 2A and 2B are a sectional view and a perspective view showing a micro robot driving system having a gear tooth shaped belt as a second embodiment in accordance with the present invention.

As shown in FIGS. 2A and 2B, a tooth shaped belt 7 is used as the movement means of the micro robot driving system, instead of the worm gear 2. The tooth shaped belt 7 is fixed rotatably in the body 6 protruding the respective slots 6a of the body. Here, the gear tooth shaped belt 7 is also positioned in gear with the worm 1 so that it can receive the upright rotational movement of the worm 1 and convert the movement of the micro robot into a transverse rotational movement.

On the other hand, in order to move the micro robot through passages such as the intestines in human body or bent pipes smoothly, direction conversion function is needed. With reference to the third, fourth and fifth embodiments, the micro robot with a structure enabling the direction conversion function will be described as follows.

Figure 3A:
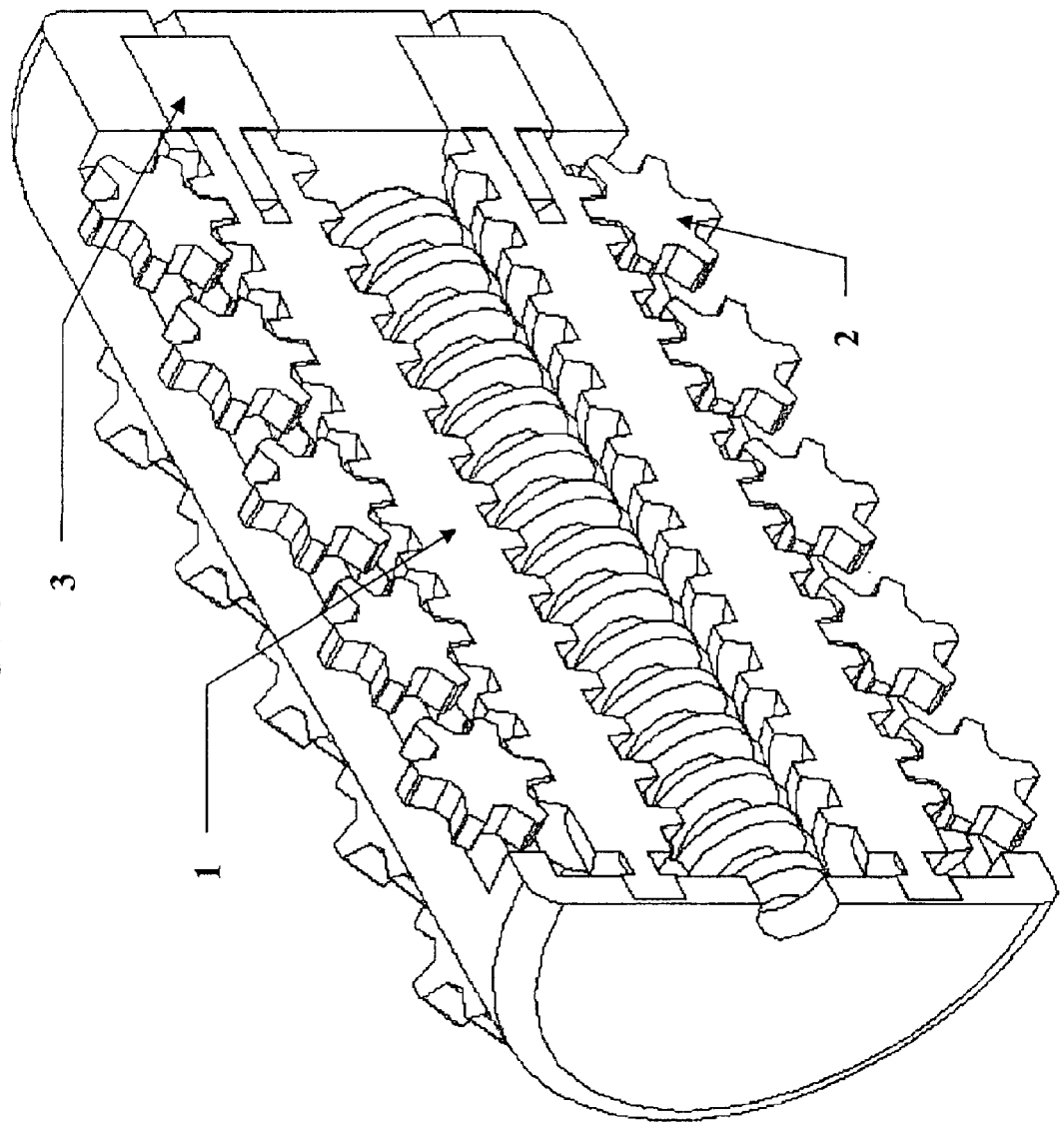
FIG. 3A is a perspective view including an end surface of a micro robot driving system having a plurality of worms as a third embodiment in accordance with the present invention.
Figure 3B:
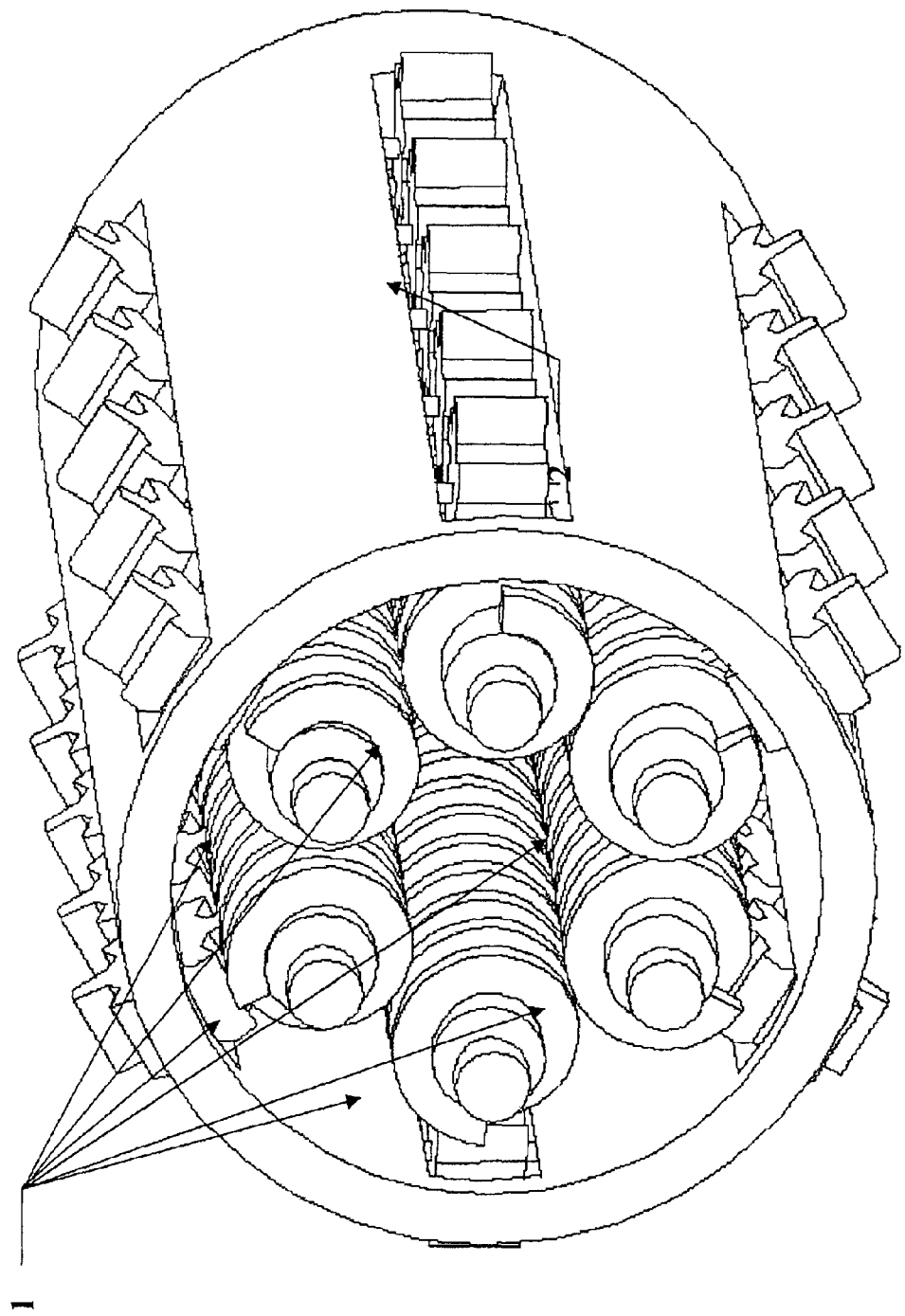
FIG. 3B is a sectional view showing a micro robot driving system having a plurality of worms as a third embodiment in accordance with the present invention.

FIGS. 3A and 3B are a perspective view and a sectional view including an end surface of a micro robot driving system having a plurality of worms as a third embodiment in accordance with the present invention.

As shown in FIGS. 3A and 3B, the rotation transmitting means comprises a plurality of worms 1 not just one worm 1, differently from the structure of the micro robot driving system of the first embodiment. Particularly, the plurality of worms 1 are driven by being connected to the respective independent driving means for driving the respective worm and positioned radially thus to rotate the worm gear 2 in gear with the respective worm gears 2 in line which is movement means.

At this time, the respective worm gears 2 in line can be rotated in the different direction and at different speeds. Therefore, by varying the speed and rotational direction of the respective worm gears 2 in line, forward, rearward and direction conversion of the body to any direction is possible. Here, the gear tooth shaped belt can be used as the movement means, instead of the worm gears 2 in line.

In case the course of the robot is radically bent, the body of the micro robot must be short to pass the micro robot properly and in case the number of the body of the micro robot is plural, the type of joint with which connection between respective bodies can be bent naturally is appropriate. A structure capable of direction conversion function in accordance with the present invention in case the number of the body of the micro robot is plural will be described as follows.

Figure 4A:
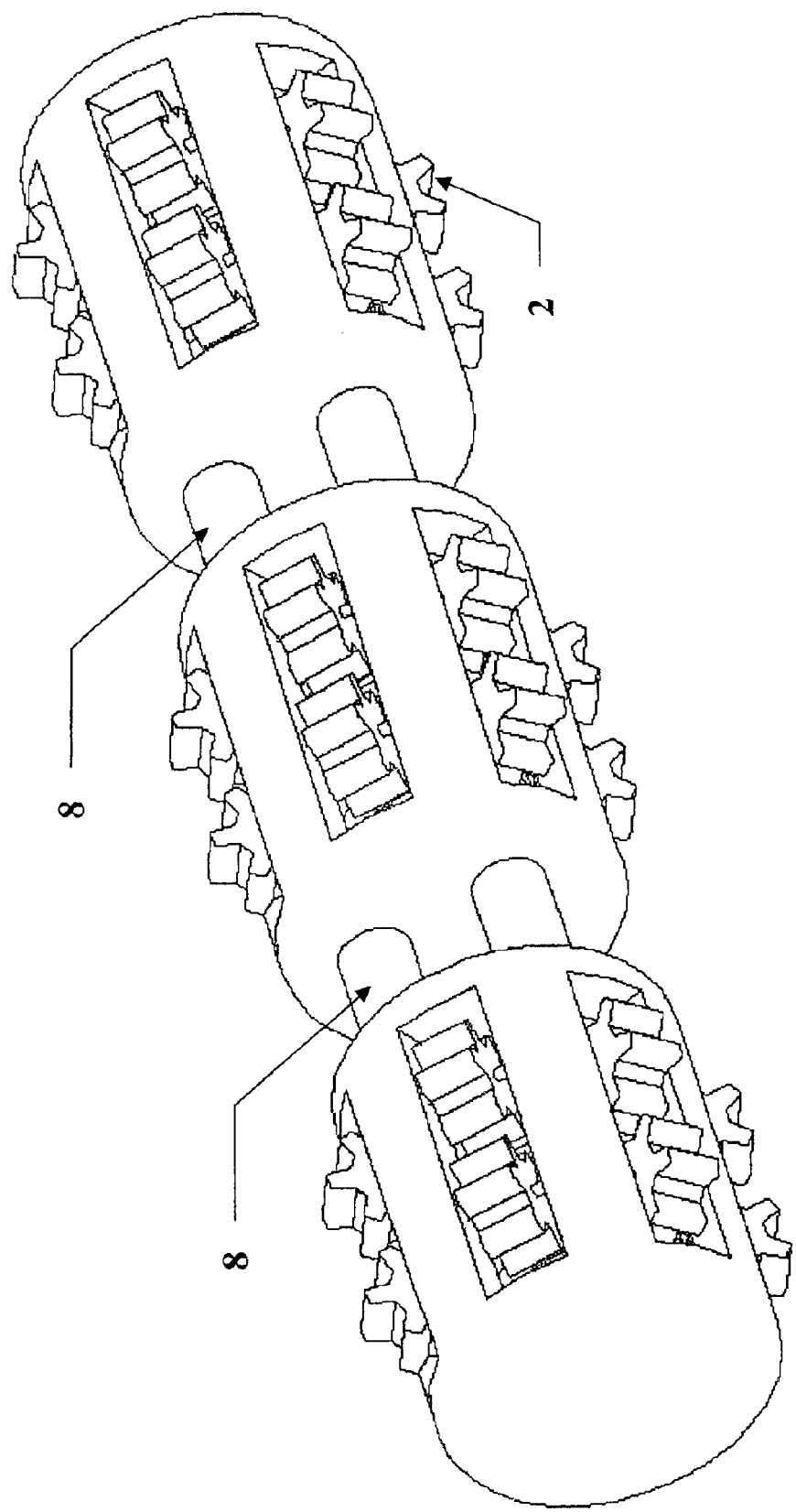
FIG. 4A is a perspective view showing a micro robot driving system having a plurality of bodies as a fourth embodiment in accordance with the present invention.
Figure 4B:
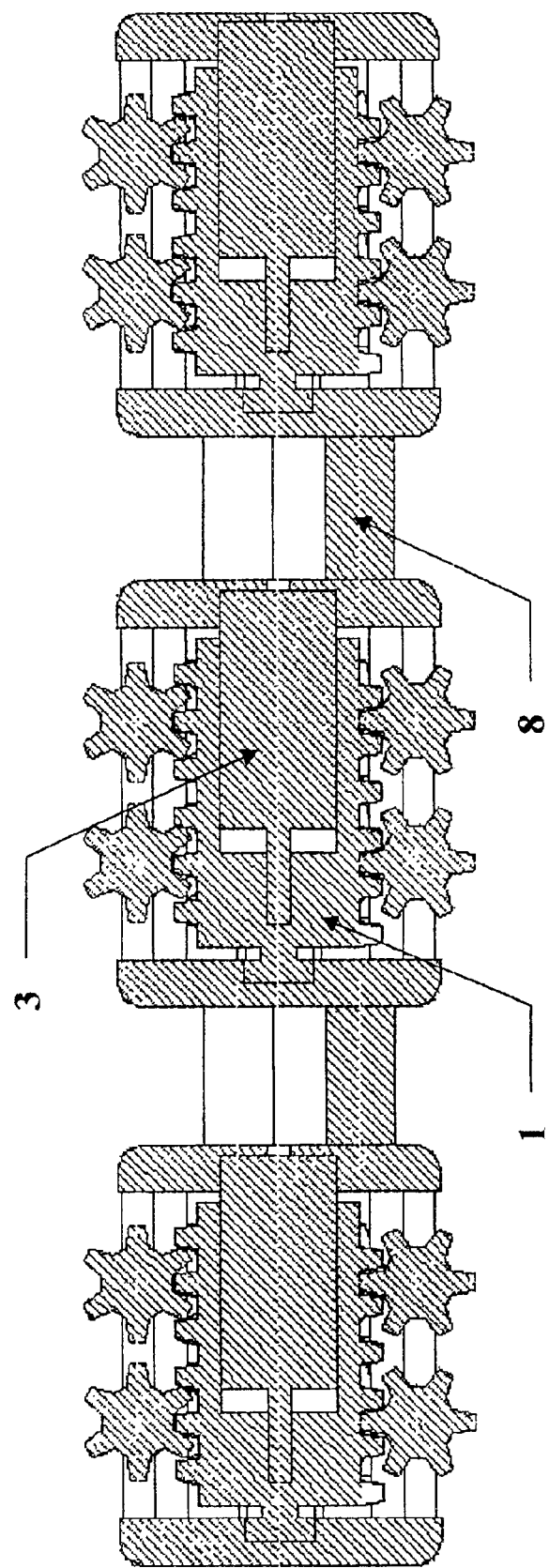
FIG. 4B is a sectional view showing a micro robot driving system having a plurality of bodies as a fourth embodiment in accordance with the present invention.
Figure 4C:
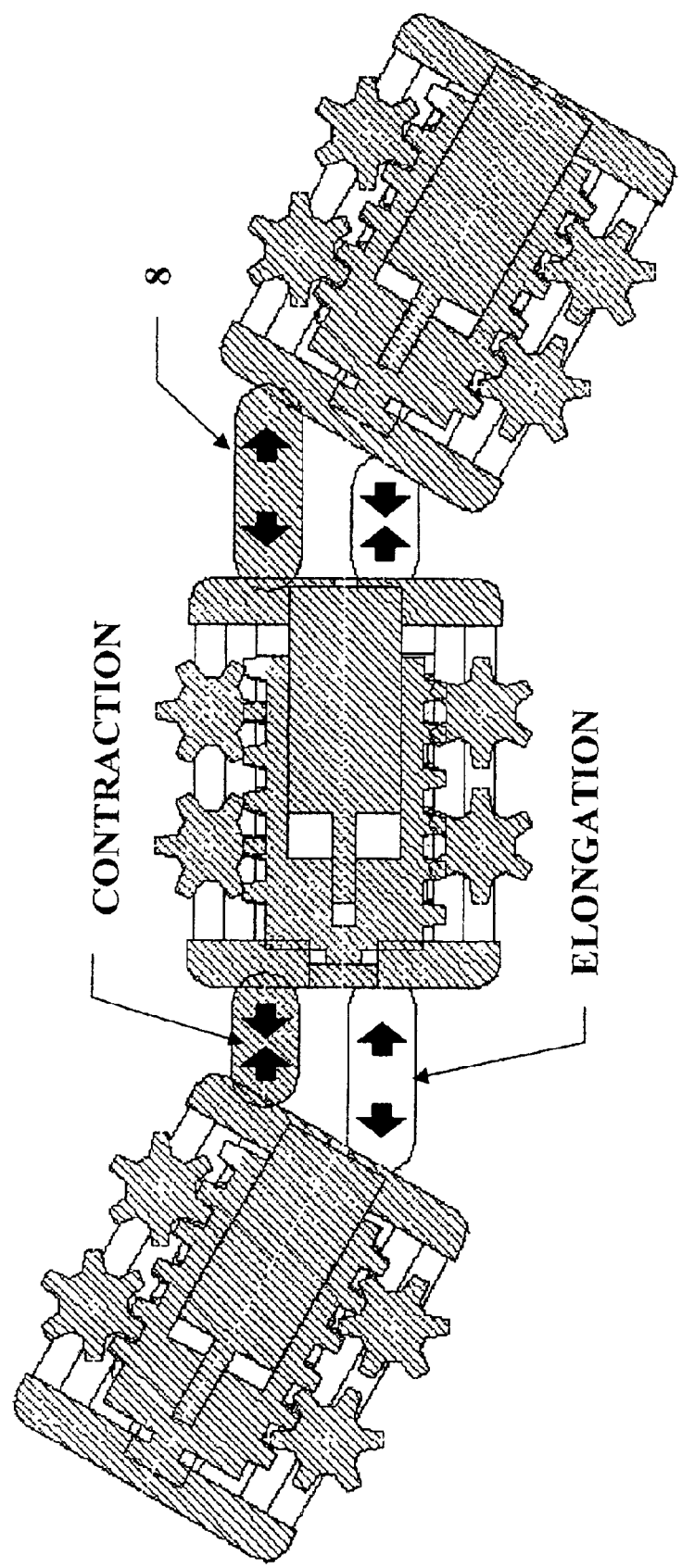
FIG. 4C is a sectional view including an operation form of a micro robot driving system having a plurality of bodies as a fourth embodiment in accordance with the present invention.

FIGS. 4A, 4B and 4C are a perspective view, a sectional view, showing a micro robot driving system having a plurality of bodies as a fourth embodiment in accordance with the present invention and a sectional view including an operation form.

As shown in FIGS. 4A, 4B and 4C, the bodies of the micro robot connected with one another comprise an independent driving apparatus 3 and worm 1, respectively. A plurality of linear actuators 8 are positioned in parallel between two bodies and connect the bodies. If the displacements of the linear actuators 8 are made different from one another, the joint part between the bodies will be bent in appropriate direction according to the difference of the displacement. In this way, the micro robot can move through bent courses.

Figure 5A:
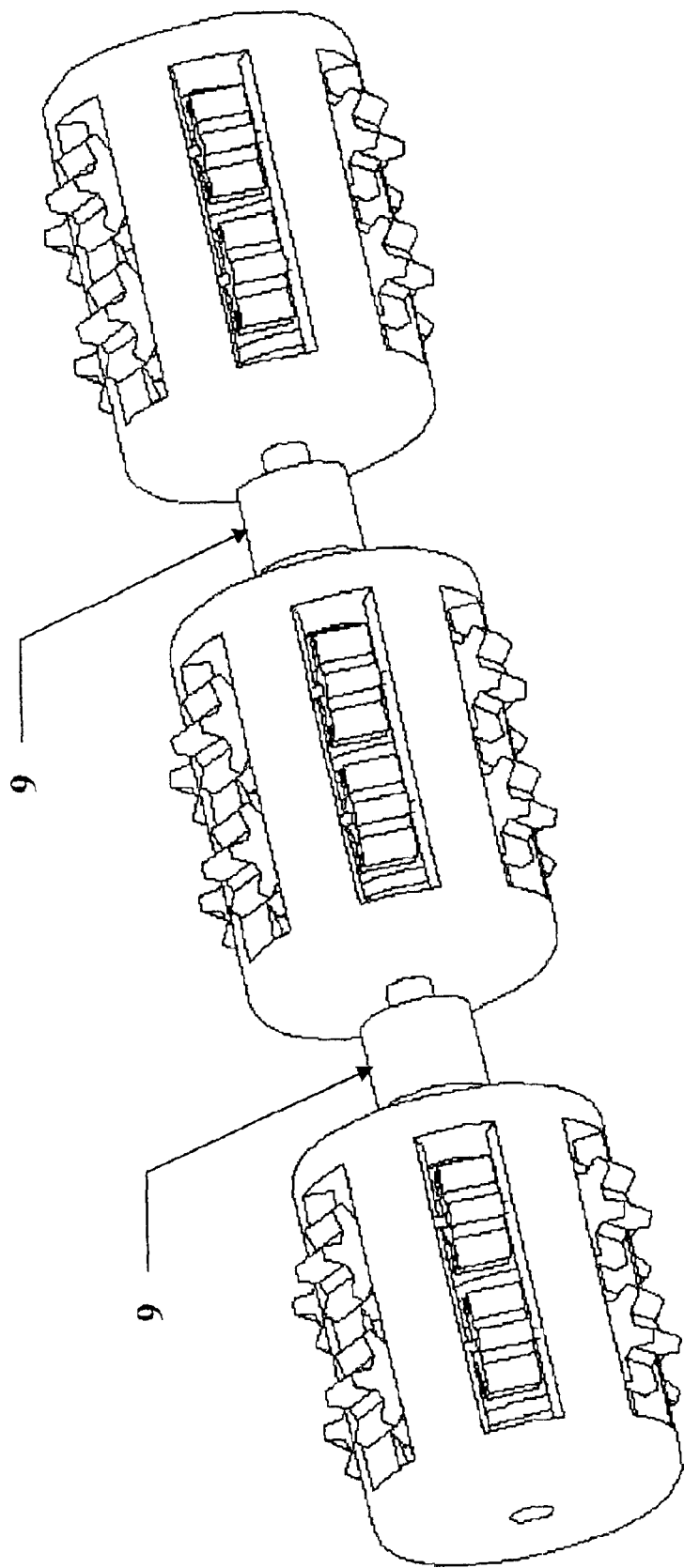
FIG. 5A is a perspective view showing a micro robot driving system having a plurality of bodies connected with a body connection means as a fifth embodiment in accordance with the present invention.
Figure 5B:
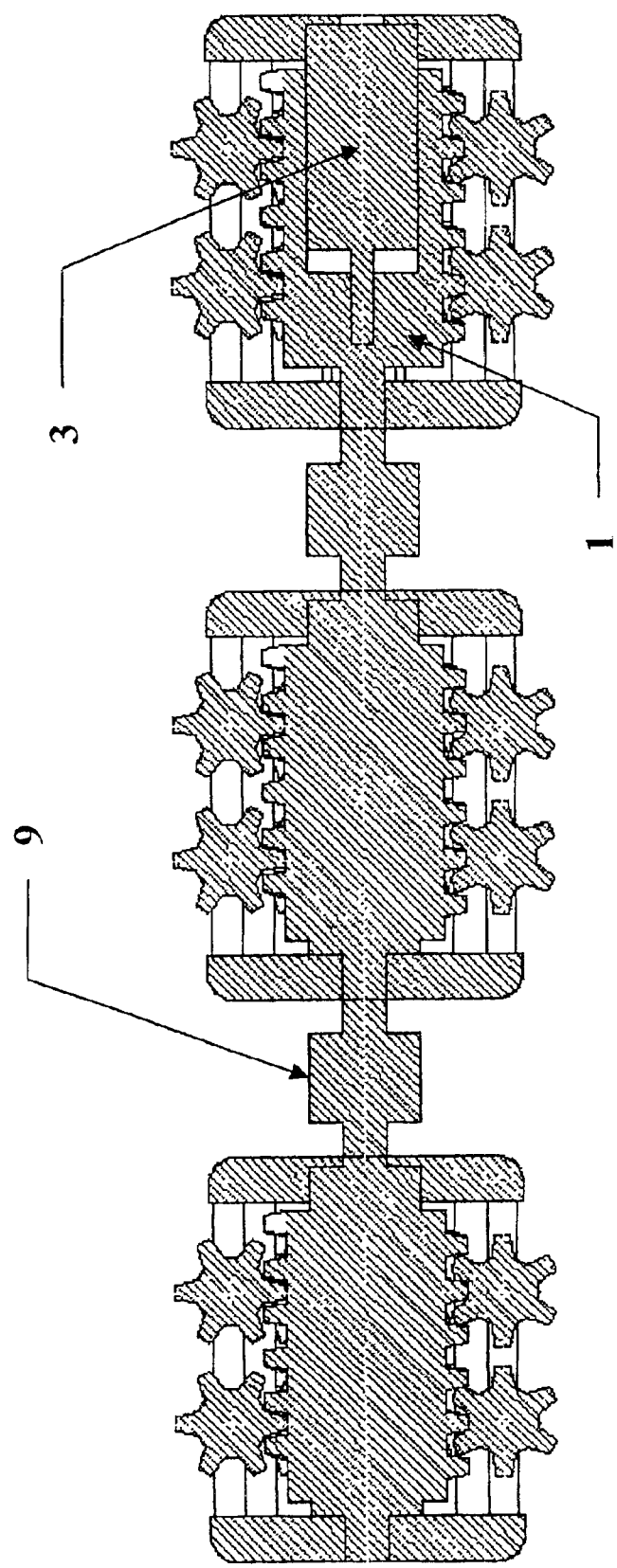
FIG. 5B is a sectional view showing a micro robot driving system having a plurality of bodies connected with a body connection means as a fifth embodiment in accordance with the present invention.

FIGS. 5A and 5B are a perspective view and a sectional view showing a micro robot driving system having a plurality of bodies connected with a body connection means as a fifth embodiment in accordance with the present invention.

As shown in FIGS. 5A and 5B, the micro robot having a plurality of bodies does not have independent driving apparatuses in the respective bodies differently from the micro robot of the fourth embodiment shown in FIGS. 4A, 4B and 4C but the micro robot has one driving apparatus 3 in one body among the plurality of bodies thus to form a structure capable of direction conversion forward, rearward or manually. The above micro robot driving system has a peculiar characteristic in the body connection means.

For example, the driving apparatus 3 is positioned in the last body of the micro robot and the rotational power of the driving apparatus 3 is transmitted to the whole bodies by the joints for connecting the worms positioned in respective bodies.

Here, the body connection means which is a joint portion to connect the respective bodies each other enables bending of respective bodies such as coupling and particularly, a coupling and transmits the rotational power transmitted from the driving apparatus 3 smoothly. Also, in the above structure, active direction conversion function can be performed by positioning the linear actuator 8 in the body connection means in parallel additionally as shown in the fourth embodiment.

For the micro robot for endoscope, a body fixing means for preventing the micro robot from shaking in case the micro robot stops in a position to perform its operation such as examining and taking tissues is needed. A method for the case is devised as follows.

Figure 6A:
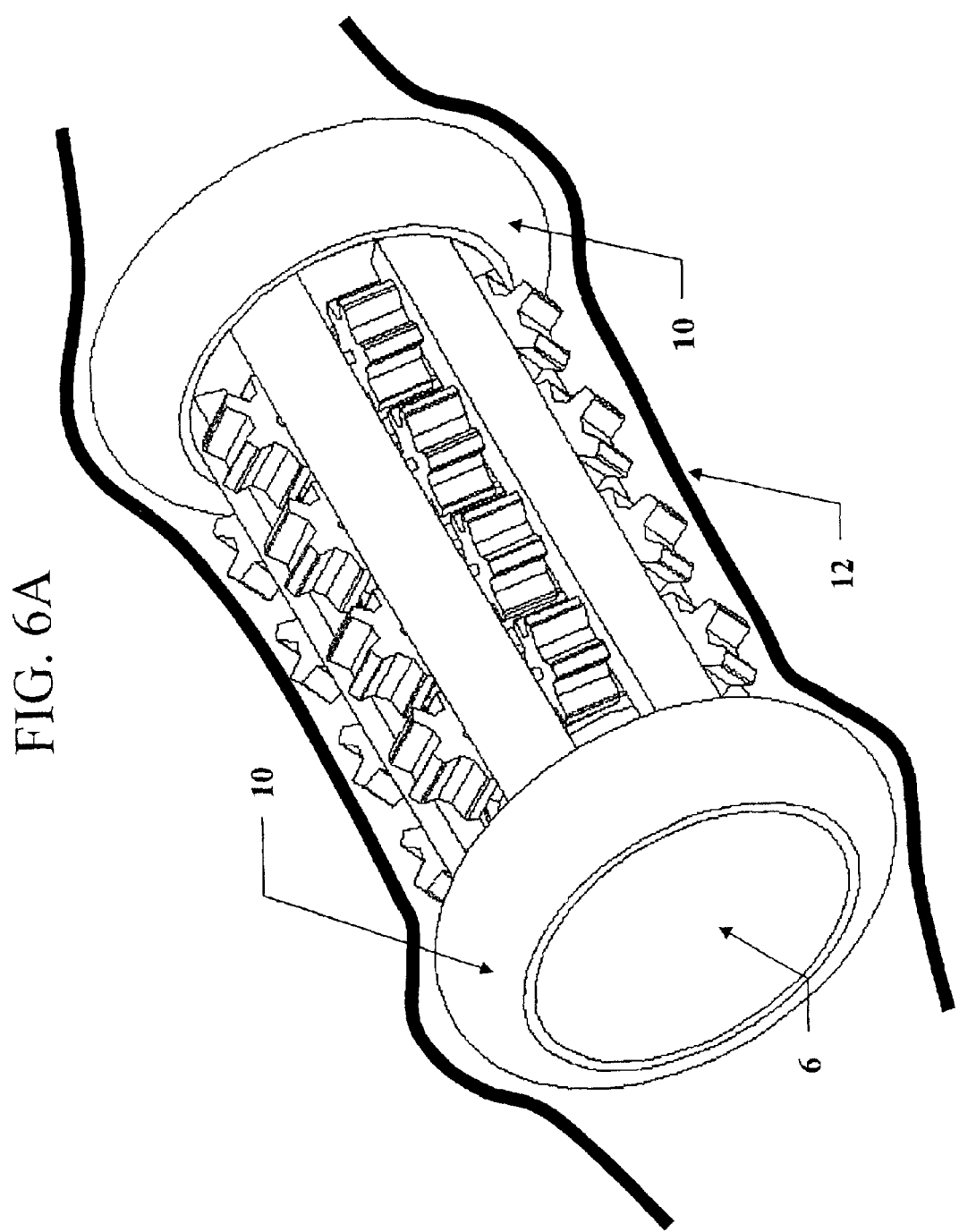
FIG. 6A shows a micro robot driving system fixed by a body fixing means as a sixth embodiment in accordance with the present invention.
Figure 6B:
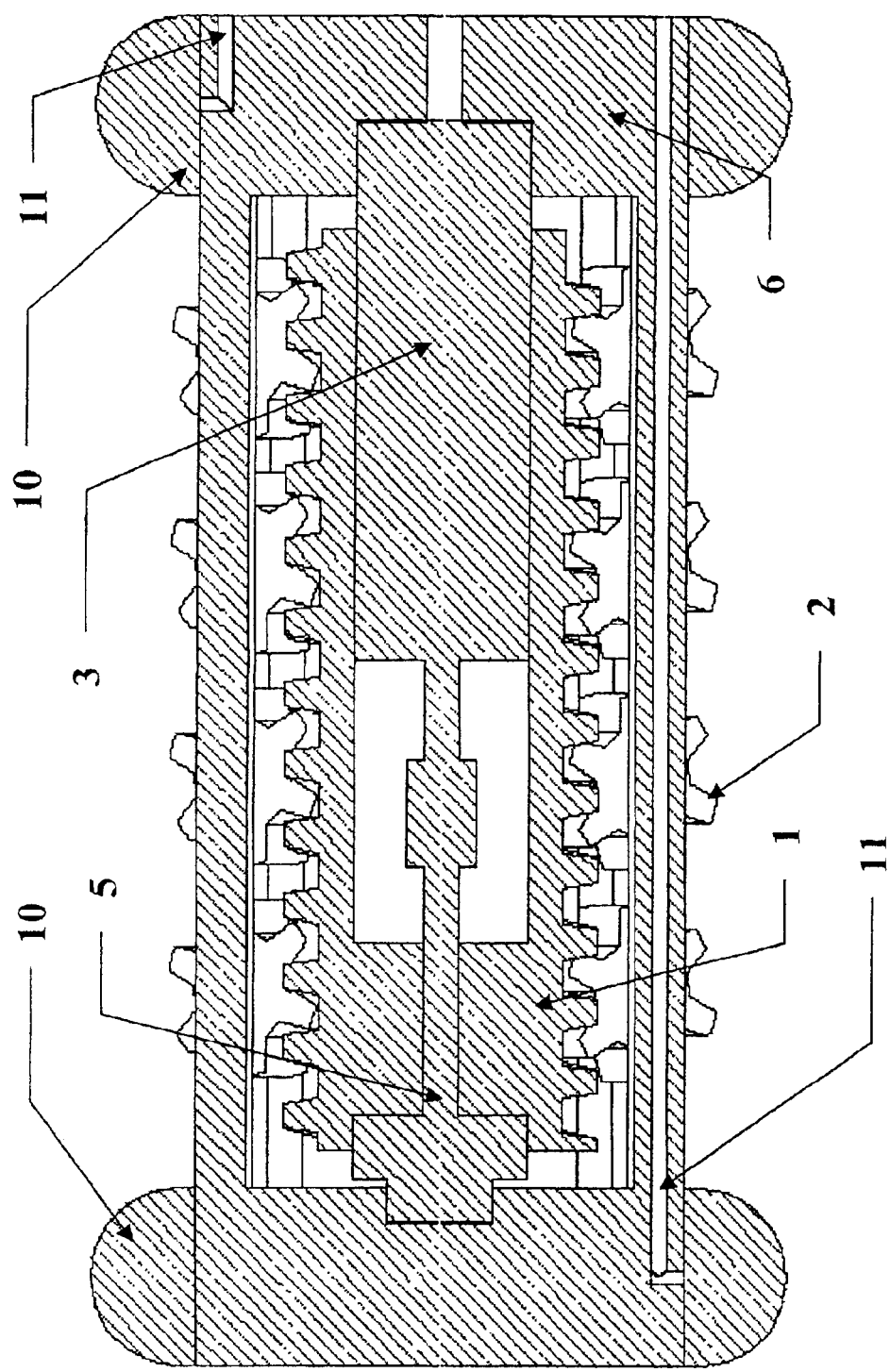
FIG. 6B is a sectional view showing a micro robot driving system fixed by a body fixing means as a sixth embodiment in accordance with the present invention.

FIG. 6A shows a micro robot driving system fixed by a body fixing means as a sixth embodiment and FIG. 6B is a sectional view showing a micro robot driving system fixed by a body fixing means as a sixth embodiment in accordance with the present invention.

As shown in FIGS. 6A and 6B, a body fixing means is included in the composition of the micro robot driving system of the first embodiment additionally. The body fixing means includes an annular pipe 10 which has a variable volume according to air pressure and an air supply line 11.

In order to perform the operation needed under the condition of being abutted and fixed to the circumferential intestines 12, in case air is injected through the air supply line 11 connected to the annular pipe 10 to protrude the micro robot body 6 by positioning the expansible annular pipe 10 on the outside of the micro robot body 6, and accordingly the annular pipe 10 is inflated, the annular pipe 10 and the intestine 11 are abutted to each other and the micro robot can stop in a position without shaking. On the contrary, if the air is flown out, the annular pipe 10 is contracted again and accordingly the micro robot can move by the rotation of the worm gear 2 or the gear tooth shaped belt 7.

The micro robot in accordance with the present invention can be used as a movement apparatus capable of moving in a pipe or rough surface as well as the endoscope used described above.

The present invention is described on the basis of the most preferred embodiments but there can be another micro robot driving systems in accordance with the disclosed claims, which are not beside the point.

As described above, the micro robot driving system in accordance with the present invention can be moved by the worm gear or the gear tooth shaped belt positioned radially using the worm thus to solve the problem of the method of the conventional inch worm type movement method that the moving circumstance affects the moving function and improve the moving function.

Also, the present invention provides the body fixing means for preventing the micro robot from shaking in case the micro robot stops in a position to perform its operation such as examining and taking tissues.

Therefore, the micro robot in accordance with the present invention can be used for endoscope or surgery for examining or diagnosing the large intestine and small intestine using a more simple and efficient structure. The manufacturing is easy, the cost can be reduced and the general size is miniaturized.

Also, the present invention can also provide a new method for a moving apparatus which can move in a pipe and rough surface as well as for a moving apparatus for endoscope.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A micro robot driving system, comprising:
    a micro robot body:
    rotational force transmitting means installed in the body, for transmitting rotational force generated by driving means;
    movement means which is connected with the rotational force transmitting means, protruded from the body for moving the body by rotational force transmitted by the rotational force transmitting means; and
    a body fixing means which is positioned at both ends of the body for fixing the body on an inner wall of intestines.

2. The system of claim 1, wherein the rotational force transmitting means is a worm.

3. The system of claim 1, wherein the rotational force transmitting means comprises a plurality of worms positioned radially with respect to a longitudinal axis of the micro robot body.

4. The system of claim 3, wherein the plurality of worms are connected with the driving means respectively.

5. The system of claim 3, wherein the plurality of worms transmit rotational force in gear with the movement means respectively.

6. The system of claim 5, wherein the movement means is worm gears in line or gear tooth shaped belt.

7. The system of claim 1, wherein the movement means is a plurality of worm gears.

8. The system of claim 1, wherein the movement means is gear tooth shaped belt.

9. The system of claim 1, wherein the movement means are positioned radially with respect to a longitudinal axis of the micro robot body.

10. The system of claim 1, wherein the rotational force transmitting means is a worm having a space inside and the driving means is positioned inside the worm.

11. The system of claim 1, wherein the driving means comprises:
    a driving apparatus having a driving shaft for generating rotational force; and
    a coupling.

12. The system of claim 1, wherein the body fixing means comprises:
    an annular pipe which has a variable volume according to air pressure covering one end of the body; and
    an air supply line for infusing air to the annular pipe or discharging air.

13. The system of claim 1, wherein a plurality of slots are formed in the body and the movement means is installed in the body protruding the slots.

14. A micro robot driving system, comprising:
    a plurality of micro robot bodies;
    rotational force transmitting means installed in the respective bodies, for transmitting rotational force generated by driving means; and
    movement means which is connected with the rotational force transmitting means, protruded from the respective bodies, for moving the respective bodies by rotational force transmitted by the rotational force transmitting means, and
    body fixing means respectively positioned at both ends of each of the micro robot bodies for fixing the respective bodies on an inner wall of intestines;
    wherein the respective bodies are connected by body connection means to each other.

15. The system of claim 14, wherein the body connection means comprises a plurality of linear driving means which are connected in a parallel with the respective bodies.

16. The system of claim 15, wherein the driving means is installed in one of the bodies and the body connection means further comprises a universal joint.

17. The system of claim 14, wherein the driving means is installed in one of the bodies and the body connection means comprises a coupling.

18. The system of claim 14, wherein the driving means is installed in one of the bodies and the body connection means comprises a universal joint.

* * * * *